United States Patent
Parks et al.

(10) Patent No.: US 10,899,751 B2
(45) Date of Patent: Jan. 26, 2021

(54) COMPOUNDS, COMPOSITIONS, AND METHODS FOR INCREASING CFTR ACTIVITY

(71) Applicant: Proteostasis Therapeutics, Inc., Boston, MA (US)

(72) Inventors: Daniel Parks, Pepperell, MA (US); Cecilia M. Bastos, South Grafton, MA (US); Matthew Cullen, Braintree, MA (US); Benito Munoz, Newtonville, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

(21) Appl. No.: 16/311,397

(22) PCT Filed: Jun. 21, 2017

(86) PCT No.: PCT/US2017/038521
§ 371 (c)(1),
(2) Date: Dec. 19, 2018

(87) PCT Pub. No.: WO2017/223188
PCT Pub. Date: Dec. 28, 2017

(65) Prior Publication Data
US 2020/0010461 A1    Jan. 9, 2020

Related U.S. Application Data

(60) Provisional application No. 62/352,672, filed on Jun. 21, 2016.

(51) Int. Cl.
C07D 261/18    (2006.01)
C07D 413/12    (2006.01)
A61P 11/00     (2006.01)
A61K 45/06     (2006.01)

(52) U.S. Cl.
CPC ............ C07D 413/12 (2013.01); A61K 45/06 (2013.01)

(58) Field of Classification Search
CPC ...................... C07D 261/18; C07D 413/12
See application file for complete search history.

(56) References Cited

U.S. PATENT DOCUMENTS

| | | |
|---|---|---|
| 5,780,393 A | 7/1998 | Newton |
| 5,888,941 A | 3/1999 | Bartroli et al. |
| 7,846,951 B2 | 12/2010 | Miller et al. |
| 7,915,297 B2 | 3/2011 | Cho et al. |
| 7,981,935 B2 | 7/2011 | Olson et al. |
| 8,193,225 B2 | 6/2012 | Schneider et al. |
| 8,236,838 B2 | 8/2012 | Jones et al. |
| 8,623,860 B2 | 1/2014 | Fleck et al. |
| 8,815,924 B2 | 8/2014 | Dorsch et al. |
| 9,745,292 B2 | 8/2017 | Bastos et al. |
| 9,790,219 B2 | 10/2017 | Bastos et al. |
| 10,017,503 B2 | 7/2018 | Bastos et al. |
| 10,174,014 B2 | 1/2019 | Bastos et al. |
| 10,344,023 B2 | 7/2019 | Bastos et al. |
| 10,392,372 B2 | 8/2019 | Bastos et al. |
| 10,392,378 B2 | 8/2019 | Bastos et al. |
| 10,548,878 B2 | 2/2020 | Munoz et al. |
| 10,550,106 B2 | 2/2020 | Munoz et al. |
| 10,662,207 B2 | 5/2020 | Munoz et al. |
| 2006/0041006 A1 | 2/2006 | Ibrahim et al. |
| 2006/0100226 A1 | 5/2006 | Sikorski et al. |
| 2008/0090882 A1 | 4/2008 | Dorsch et al. |
| 2009/0069288 A1 | 3/2009 | Breinlinger et al. |
| 2009/0163545 A1 | 6/2009 | Goldfarb |
| 2009/0264486 A1 | 10/2009 | Jones et al. |
| 2009/0318429 A1 | 12/2009 | Doyle et al. |
| 2010/0234367 A1 | 9/2010 | Nomura et al. |
| 2011/0003784 A1 | 1/2011 | Garvey et al. |
| 2011/0082181 A1 | 4/2011 | Seiders et al. |
| 2011/0212975 A1 | 9/2011 | Kao et al. |
| 2012/0095002 A1 | 4/2012 | Ratcliffe et al. |
| 2012/0264738 A1 | 10/2012 | Sugimoto et al. |
| 2013/0217883 A1 | 8/2013 | Adaway |
| 2013/0237502 A1 | 9/2013 | Curtis et al. |
| 2014/0073667 A1 | 3/2014 | Morgan |
| 2014/0364467 A1 | 12/2014 | Schneider et al. |
| 2016/0151335 A1 | 6/2016 | Tait et al. |
| 2017/0001991 A1 | 1/2017 | Bastos et al. |
| 2017/0001993 A1 | 1/2017 | Bastos et al. |
| 2017/0233379 A1 | 8/2017 | Bastos et al. |
| 2017/0362214 A1 | 12/2017 | Bastos et al. |

(Continued)

FOREIGN PATENT DOCUMENTS

| | | |
|---|---|---|
| CA | 2736441 A1 | 10/2012 |
| EP | 0337263 A2 | 10/1989 |

(Continued)

OTHER PUBLICATIONS

Jain, "Beyond the Lungs: How CFTR modulators benefit cystic fibrosis patients" p. 1-7. (Retrieved from the Internet at: https://utswmed.org/medblog/cftr-modulators-cystic-fibrosis/ on Feb. 27, 2020.) (Year: 2018).* Lopes-Pacheco, Frontiers in Pharmacology, vol. 10, p. 1-29 (Year: 2020).*
"AID 775-Screen for Chemicals that Extend Yeast Lifespan," PubChem, 1-11 (Jul. 12, 2007), XP055331102.
Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands," Journal of Medicinal Chemistry, 57:10 4239-4251(2014), XP002754990.

(Continued)

*Primary Examiner* — Emily A Bernhardt
(74) *Attorney, Agent, or Firm* — Goodwin Procter LLP

(57) ABSTRACT

The present disclosure is directed to disclosed compounds that increase cystic fibrosis transmembrane conductance regulator (CFTR) activity as measured in human bronchial epithelial (hBE) cells.

17 Claims, No Drawings

(56) References Cited

U.S. PATENT DOCUMENTS

| | | | |
|---|---|---|---|
| 2017/0369480 | A1 | 12/2017 | Bastos et al. |
| 2017/0369482 | A1 | 12/2017 | Bastos et al. |
| 2018/0127400 | A1 | 5/2018 | Bastos et al. |
| 2018/0147187 | A1 | 5/2018 | Bastos et al. |
| 2018/0214419 | A1 | 8/2018 | Munoz et al. |
| 2018/0291006 | A1 | 10/2018 | Munoz et al. |
| 2018/0327363 | A1 | 11/2018 | Bastos et al. |
| 2018/0369209 | A1 | 12/2018 | Miller et al. |
| 2019/0022071 | A1 | 1/2019 | Lee |
| 2019/0154661 | A1 | 5/2019 | Miller et al. |
| 2019/0308960 | A1 | 10/2019 | Bastos et al. |
| 2020/0010461 | A1 | 1/2020 | Parks et al. |

FOREIGN PATENT DOCUMENTS

| | | | |
|---|---|---|---|
| EP | 0957099 | A2 | 11/1999 |
| WO | WO-2002000651 | A2 | 1/2002 |
| WO | WO-2003093297 | A2 | 11/2003 |
| WO | WO-2005035514 | A2 | 4/2005 |
| WO | WO-2005077345 | A1 | 8/2005 |
| WO | WO-2005077373 | A2 | 8/2005 |
| WO | WO-2006014134 | A1 | 2/2006 |
| WO | WO-2006136924 | A1 | 12/2006 |
| WO | WO-2007075896 | A2 | 7/2007 |
| WO | WO-2007078113 | A1 | 7/2007 |
| WO | WO-2007086584 | A1 | 8/2007 |
| WO | WO-2007126362 | A1 | 11/2007 |
| WO | WO-2008046072 | A2 | 4/2008 |
| WO | WO-2008051757 | A1 | 5/2008 |
| WO | WO-2008070739 | A1 | 6/2008 |
| WO | WO-2009005269 | A2 | 1/2009 |
| WO | WO-2009011850 | A2 | 1/2009 |
| WO | WO-2009016241 | A1 | 2/2009 |
| WO | WO-2010089297 | A1 | 8/2010 |
| WO | WO-2010142801 | A1 | 12/2010 |
| WO | WO-2011008931 | A2 | 1/2011 |
| WO | WO-2012007500 | A2 | 1/2012 |
| WO | WO-2012158885 | A1 | 11/2012 |
| WO | WO-2013019561 | A1 | 2/2013 |
| WO | WO-2013146970 | A1 | 10/2013 |
| WO | WO-2014144860 | A1 | 9/2014 |
| WO | WO-2014181287 | A1 | 11/2014 |
| WO | WO-2014210159 | A1 | 12/2014 |
| WO | WO-2015051230 | A1 | 4/2015 |
| WO | WO-2015138909 | A1 | 9/2015 |
| WO | WO-2015138934 | A1 | 9/2015 |
| WO | WO-2015196071 | A1 | 12/2015 |
| WO | WO-2016054560 | A1 * | 4/2016 ............ A61K 31/42 |
| WO | WO-2016105468 | A1 | 6/2016 |
| WO | WO-2016105477 | A1 | 6/2016 |
| WO | WO-2016105484 | A1 | 6/2016 |
| WO | WO-2016105485 | A2 | 6/2016 |
| WO | WO-2016115090 | A1 | 7/2016 |
| WO | WO-2017019589 | A1 | 2/2017 |
| WO | WO-2017062581 | A1 | 4/2017 |
| WO | WO-2017112853 | A1 | 6/2017 |

OTHER PUBLICATIONS

CAS Registry No. 797781-85-2 (available Dec. 15, 2004).
Chang, X., "3-(2-chlorophenyl)-N-methylisoxazole-5-Carboxamide," ACTA Crystallographica, Section E: Structure Reports Online, vol. E63(7), pp. 03074-sup-7 (2007).
Compound Summary for CID 70741394, Pubchem: Create Date: Mar. 4, 2013 [retrieved on May 12, 2015].
Compound Summary for CID 70756362, Pubchem: Create Date: Mar. 4, 2013 [retrieved on May 12, 2015].
Compound Summary for: CID 36257620, Pubchem: Create Date: May 29, 2009 [retrieved on May 12, 2015].
Compound Summary for: CID 55795703, Pubchem: Create Date: Jan. 25, 2012 [retrieved on May 12, 2015].
Demina et al., "5-substituted Pyridylisoxazoles as Effective Inhibitors of Platelet Aggregation," Russian Chemical Bulletin, International Edition, vol. 63(2) 2095-2113 (2014).
International Search Report and Written Opinion for International Application No. PCT/US2014/044100, dated Oct. 10, 2014, 8 pages.
International Search Report and Written Opinion for International Application No. PCT/US2015/000189, dated Mar. 18, 2016, 10 pages.
International Search Report and Written Opinion for International Application No. PCT/US2015/000202, dated Mar. 22, 2016, 8 pages.
International Search Report and Written Opinion for International Application No. PCT/US2015/000211, dated Mar. 29, 2016, 10 pages.
International Search Report and Written Opinion for International Application No. PCT/US2015/000212, dated Jul. 1, 2016, 22 pages.
International Search Report and Written Opinion for International Application No. PCT/US2015/020460, dated Jun. 9, 2015, 7 pages.
International Search Report and Written Opinion for International Application No. PCT/US2015/020499, dated Jun. 9, 2015, 8 pages.
International Search Report and Written Opinion for International Application No. PCT/US2015/036691, dated Aug. 20, 2015, 12 pages.
International Search Report and Written Opinion for International Application No. PCT/US2016/012982, dated Mar. 7, 2016, 12 pages.
International Search Report and Written Opinion for International Application No. PCT/US2016/043835, dated Oct. 10, 2016, 8 pages.
International Search Report and Written Opinion for International Application No. PCT/US2016/068266, dated Feb. 27, 2017, 11 pages.
International Search Report and Written Opinion for International Application No. PCT/US2017/026579, dated Jun. 6, 2017, 9 pgs.
International Search report and Written Opinion for International Application No. PCT/US2017/040606, dated Nov. 30, 2016, 10 pages.
Kalid et al., "Small Molecule Correctors of F508del-CFTR Discovered by Structure-based Virtual Screening," Journal of Computer-Aided Molecular Design, vol. 24:971-991 (2010).
Lack et al., "Targeting the Binding Function 3 (BF3) Site of the Human Androgen Receptor through Virtual Screening," Journal of Medicinal Chemistry, vol. 54(24) 8563-8573 (2011).
Liedtke, W., "Role of TRPV ion Channels in Sensory Transduction of Osmotic Stimuli in Mammals," Experimental Physiology, 92:3 507-512 (2007) XP055252392.
Lukevics et al.,"Synthesis and Cytotoxicity of Silyl- and Carbonyl-substituted Isoxazoles,"Chemistry of Heterocyclic Compounds, Springer New York LLC, vol. 36(10); 1226-1231 (1995).
Munchhof et al., "Discovery of PF-04449913, a Potent and Orally Bioavailable Inhibitor of Smoothened," ACS Medicinal Chemistry Letters, vol. 3(2) 106-111 (2012).
Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.
Pubchem: "ST062658 | C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].
Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).
Showell et al., "Chemistry Challenges in Lead Optimization: Silicon Isosteres in Drug Discovery," Drug Discovery Today 8: 551-556 (2003).
Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).
Supplemental European Search Report dated Jan. 9, 2017 in European Patent No. 14816975.8 (19 pages).

(56) References Cited

OTHER PUBLICATIONS

U.S. Appl. No. 15/542,997, "Compounds, Compositions, and Methods for Increasing CFTR Activity," filed Jul. 12, 2017 (175 pages).
U.S. Appl. No. 15/653,934, "Compounds, Compositions, and Methods for Increasing CFTR Activity," filed Jul. 19, 2017 (76 pages).
U.S. Appl. No. 15/697,901, "Compounds, Compositions, and Methods for Increasing CFTR Activity," filed Sep. 7, 2017 (112 pages).
U.S. Appl. No. 16/716,765, "Compounds, Compositions, and Methods for Modulating CFTR," filed Dec. 17, 2019 (310 pages).
International Search Report and Written Opinion for International Application No. PCT/US2018/030123, dated Jul. 9, 2018, 10 pgs.

* cited by examiner

COMPOUNDS, COMPOSITIONS, AND METHODS FOR INCREASING CFTR ACTIVITY

CROSS REFERENCE TO RELATED APPLICATIONS

This application is a national stage filing under 35 U.S.C. § 371 of PCT/US2017/038521, filed Jun. 21, 2017, which claims the benefit of, and priority to, U.S. provisional application No. 62/352,672, filed Jun. 21, 2016; the contents of which are hereby incorporated by reference herein in their entirety.

BACKGROUND

Cells normally maintain a balance between protein synthesis, folding, trafficking, aggregation, and degradation, referred to as protein homeostasis, utilizing sensors and networks of pathways (Sitia et al., Nature 426: 891-894, 2003; Ron et al., Nat Rev Mol Cell Biol 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., Cell 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., Science 319, 916-9 (2008); Powers, et al., Annu Rev Biochem 78, 959-91 (2009); Hutt et al., FEBS Lett 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., Annu Rev Biochem 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., J Biol Chem 272, 15739-44 (1997)). The loss of a functional CFTR channel at the plasma membrane disrupts ionic homeostasis (Cl$^-$, Na$^+$, HCO$_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, J Intern Med 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, cholestatic liver disease (e.g. Primary biliary cirrhosis (PBC) and primary sclerosing cholangitis (PSC)) (Sloane et al. (2012), PLoS ONE 7(6): e39809.doi: 10.1371/journal.pone.0039809; Bombieri et al. (2011), J Cyst Fibros. 2011 June; 10 Suppl 2:S86-102; (Albert et al. (2008), Clinical Respiratory Medicine, Third Ed., Mosby Inc.; Levin et al. (2005), Invest Ophthalmol Vis Sci., 46(4): 1428-34; Froussard (2007), Pancreas 35(1): 94-5), Son et al. (2017) J Med Chem 60(6):2401-10.

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds such as those having disclosed formulas) can increase cystic fibrosis transmembrane conductance regulator (CFTR) activity as measured in human bronchial epithelial (hBE) cells.

For example, disclosed herein are compounds represented by formula I or II:

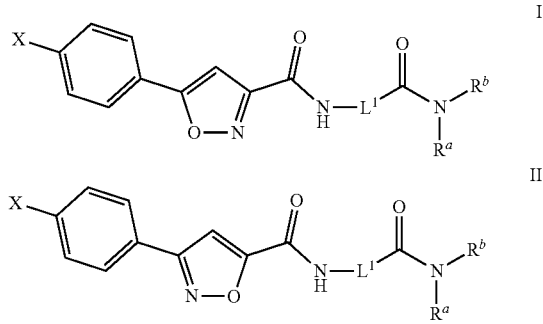

and pharmaceutically acceptable salts, stereoisomers, and prodrugs thereof, wherein:

X is selected from the group consisting of hydrogen and halogen;

L$^1$ is selected from the group consisting of C$_{3-6}$cycloalkylene and C$_{1-6}$alkylene; and R$^a$ and R$^b$ are each independently selected from the group consisting of hydrogen, C$_{1-4}$alkyl and C$_{3-6}$cycloalkylene (optionally substituted by methyl, ethyl, or carboxyl); or R$^a$ and R$^b$ taken together with the nitrogen to which they are attached form a 4-6 membered heterocyclic ring, optionally substituted on additional ring nitrogen if present or on a ring carbon, by a C$_{1-6}$ alkyl such as methyl or ethyl.

Also contemplated herein are pharmaceutical compositions that include a disclosed compound (such as those compounds having disclosed formulas such as Formula I or II) and a pharmaceutically acceptable carrier or excipient. In certain embodiments, the compositions can include at least one additional CFTR modulator as described anywhere herein or at least two additional CFTR modulators, each independently as described anywhere herein.

In additional embodiments, a method of enhancing (e.g., increasing) cystic fibrosis transmembrane conductance regulator (CFTR) activity in a subject in need thereof is provided comprising administering to said subject an effective amount of a disclosed compound of e.g., Formula I or II.

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, E56K, P67L, R74W, D110E, D110H, R117C, G178R, E193K, L206W, R347H, R352Q, A455E, S549R, G551S, D579G, S945L, S997F, F1052V, K1060T, A1067T, G1069R, R1070Q, R1070W, F1074L, G1244E, S1251N, S1255P, D1270N, G1349D, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X; Δ508F) are enhanced (e.g., increased).

In certain embodiments, a method is provided comprising administering a disclosed compound to a subject (e.g., a human patient) suffering from a disease associated with decreased CFTR activity (e.g., cystic fibrosis, congenital bilateral absence of vas deferens (CBAVD), acute, recurrent, or chronic pancreatitis, disseminated bronchiectasis, asthma, allergic pulmonary aspergillosis, chronic obstructive pulmonary disease (COPD), chronic sinusitis, dry eye disease, protein C deficiency, A-β-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, Sjogren's syndrome, familial hypercholesterolemia, I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, nephrogenic DI, Charcot-Marie Tooth syndrome, Perlizaeus-Merzbacher disease, Alzheimer's disease, Parkinson's disease, amyotrophic lateral sclerosis, progressive supranuclear palsy, Pick's disease, Huntington's disease, spinocerebellar ataxia type I, spinal and bulbar muscular atrophy, dentatorubral pallidoluysian, myotonic dystrophy, hereditary Creutzfeldt-Jakob disease (due to prion protein processing defect), Fabry disease, cholestatic liver disease (e.g. Primary biliary cirrhosis (PBC) and primary sclerosing cholangitis (PSC)), and Straussler-Scheinker syndrome). In certain embodiments, the disease is cystic fibrosis.

Also contemplated herein is a method for treating a patient suffering from cystic fibrosis comprising administering to said patient an effective amount of a disclosed compound.

In some embodiments, the methods described herein can further include administering an additional CFTR modulator or administering at least two additional CFTR modulators. In certain embodiments, at least one CFTR modulator is a CFTR corrector (e.g., VX-809 (lumacaftor), VX-661 (tezacaftor), VX-983, VX-152, VX-440, VX-445, VX-659, GLPG2851, GLPG2665, GLPG2737, GLPG3221, or GLPG2222) or potentiator (e.g., ivacaftor GLPG1837, GLPG2545, GLPG3067 and/or genistein). In certain of these embodiments, one of the at least two additional therapeutic agents is a CFTR corrector (e.g., VX-809, VX-661, VX-983, VX-152, VX-440, VX-445, VX-659, GLPG2222, GLPG3221, GLPG2737, GLPG2851 and/or GLPG2665) and the other is a CFTR potentiator (e.g., ivacaftor, GLPG1837, GLPG2545, GLPG3067, and/or genistein).

DETAILED DESCRIPTION

As used herein, the words "a" and "an" are meant to include one or more unless otherwise specified. For example, the term "an agent" encompasses both a single agent and a combination of two or more agents.

As discussed above, the present disclosure is directed in part to compounds as described herein or a pharmaceutically acceptable salt, prodrug or solvate thereof, pharmaceutical compositions, methods of increasing CFTR activity and methods of treating cystic fibrosis.

For example, disclosed herein are compounds represented by formula I or II:

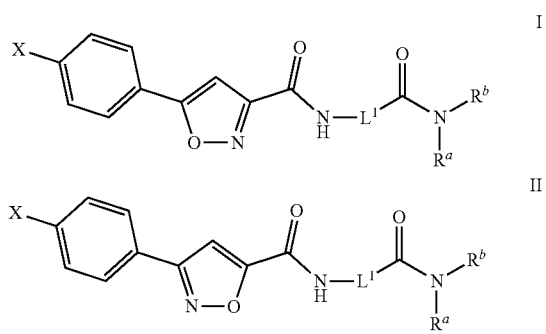

and pharmaceutically acceptable salts, stereoisomers, and prodrugs thereof, wherein:

X is selected from the group consisting of hydrogen and halogen;

$L^1$ is selected from the group consisting of $C_{3-6}$cycloalkylene and $C_{1-6}$alkylene; and $R^a$ and $R^b$ are each independently selected from the group consisting of hydrogen, $C_{1-4}$alkyl and $C_{3-6}$cycloalkylene (optionally substituted by methyl, ethyl, or carboxyl); or $R^a$ and $R^b$ taken together with the nitrogen to which they are attached form a 4-6 membered heterocyclic ring, optionally substituted on additional ring nitrogen if present or on a ring carbon, by methyl or ethyl.

In certain embodiments, $L^1$ may be, for example, $C_4$cycloalkylene. For example, compounds disclosed herein my be represent by formula III or IV:

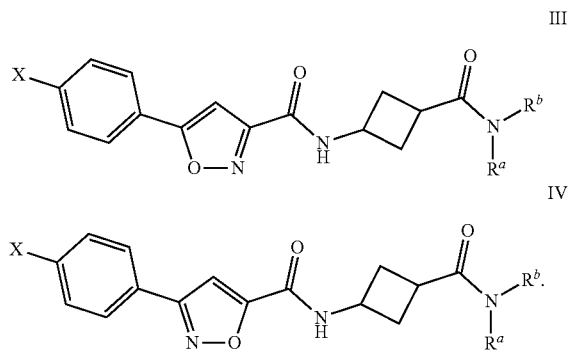

In certain other embodiments, $L^1$ may be, for example, $C_3$alkylene. For example, compounds disclosed herein my be represent by formula Va, VIa, Vb, VIb:

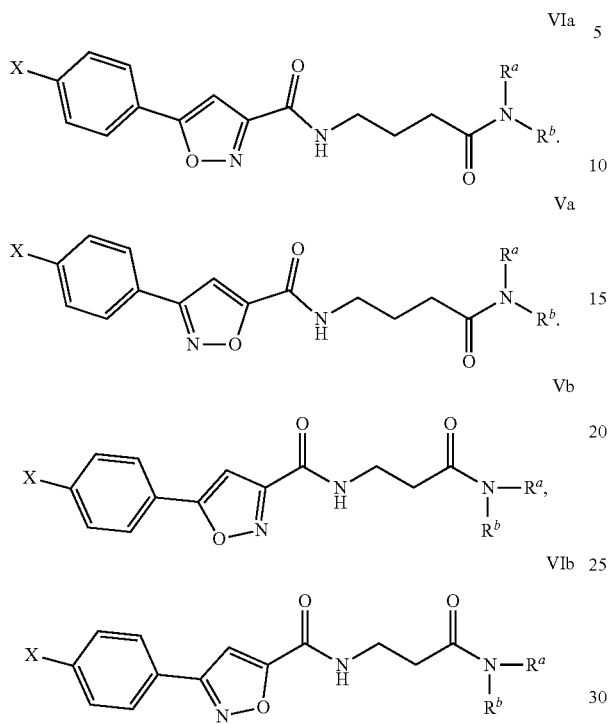

In certain embodiments X may hydrogen. In certain other embodiments, X may be fluorine.

In certain embodiments, $R^a$ and $R^b$ taken together with the nitrogen to which they are attached form a 4 membered heterocyclic ring, for example, and azetidine ring.

Exemplary compounds of the disclosure are shown below in Table 1a and Table 1b:

TABLE 1a

| Example # | Structure |
|---|---|
| 1 | 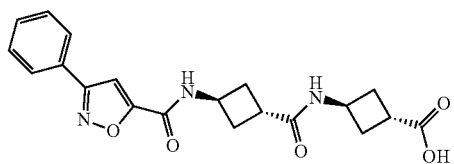 [SMILES: O=C(N[C@H]1C[C@H](C(=O)N[C@H]2C[C@H](C(=O)O)C2)C1)c1cc(-c2ccccc2)no1] |
| 2 | 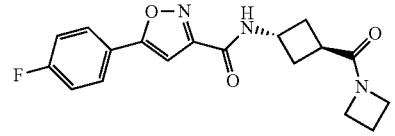 [SMILES: O=C(N[C@H]1C[C@H](C(=O)N2CCC2)C1)c1cc(-c2ccc(F)cc2)on1] |
| 3 | 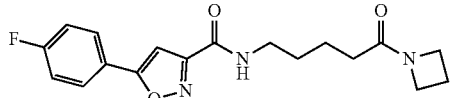 |
| 4 | 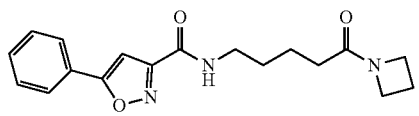 [SMILES: O=C(NCCCCC(=O)N1CCC1)c1cc(-c2ccccc2)on1] |

Additional compounds contemplated include those in Table 1B:

| | |
|---|---|
| 5 | 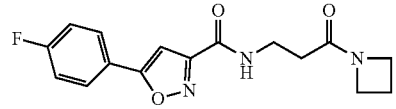 [SMILES: O=C(NCCC(=O)N1CCC1)c1cc(-c2ccc(F)cc2)on1] |
| 6 | |
| 7 | 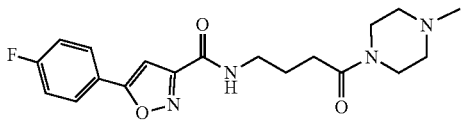 [SMILES: CN1CCN(C(=O)CCCNC(=O)c2cc(-c3ccc(F)cc3)on2)CC1] |
| 8 | |
| 9 | 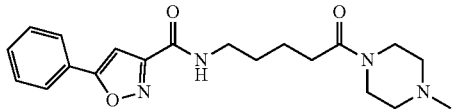 [SMILES: CN1CCN(C(=O)CCCCNC(=O)c2cc(-c3ccccc3)on2)CC1] |
| 10 | |
| 11 | |
| 12 | 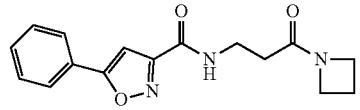 [SMILES: O=C(NCCC(=O)N1CCC1)c1cc(-c2ccccc2)on1] |

Also contemplated herein are pharmaceutical compositions that include a disclosed compound such as those compounds having Formula I or II and a pharmaceutically acceptable carrier or excipient. In certain embodiments, the compositions can include at least one additional CFTR modulator as described anywhere herein or at least two additional CFTR modulators, each independently as described anywhere herein.

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of the present disclosure herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$ alkenyl, and $C_{3-4}$ alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively for example. Examples of cycloalkyl include, but are not limited to, cyclopropyl, cyclobutyl, cyclopentyl, cyclohexyl, cycloheptyl and adamantyl.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$ alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocloalkenyl as used herein refers to cycloalkenyl groups containing one or more heteroatoms (0, S or N) within the ring. Heterobicycloalkyl refers to bicycloalkyl groups containing one or more heteroatoms (0, S or N) within a ring. Heterobicycloalkenyl as used herein refers to bicycloalkenyl groups containing one or more heteroatoms (0, S or N) within a ring, a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

Cycloalkyl, cycloalkenyl, and heterocyclic groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, naphthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In yet other embodiments, the heteroaryl is a mono or bicyclic 4- to 10-membered heteroaryl.

The term "substituted" refers to substitution by independent replacement of one, two, or three or more of the hydrogen atoms with substituents including, but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —OR$_x$, —C(O)R$_y$, —C(O)C(O)R$_y$, —OCO$_2$R$_y$, —OC(O)R$_y$, OC(O)C(O)R$_y$, —NHC(O)R$_y$, —NHCO$_2$R$_y$, —NHC(O)C(O)R$_y$, NHC(S)NH$_2$, —NHC(S)NHR$_x$, —NHC(NH)NH$_2$, —NHC(NH)NHR$_x$, —NHC(NH)R$_x$, —C(NH)NHR$_x$, and (C=NR$_x$)R$_x$; —NRxC(O)R$_x$, —NR$_x$C(O)N(R$_x$)$_2$, —NRxCO$_2$R$_y$, —NRxC(O)C(O)R$_y$, —NR$_x$C(S)NH$_2$, —NR$_x$C(S)NHR$_x$, —NR$_x$C(NH)NH$_2$, —NR$_x$C(NH)NHR$_x$, —NR$_x$C(NH)R$_x$, —C(NRx)NHR$_x$—S(O)R$_y$, —NHSO$_2$R$_x$, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -polyalkoxyalkyl, -polyalkoxy, -methoxymethoxy, -methoxyethoxy, —SH, —S—R$_x$, or -methylthiomethyl, wherein R$_x$ is selected from the group consisting of hydrogen, —C$_1$-C$_{12}$ alkyl, —C$_2$-C$_{12}$ alkenyl, —C$_2$-C$_{12}$ alkynyl, —C$_3$-C$_{12}$ cycloalkyl, -aryl, -heteroaryl and -heterocyclic and —R$_y$ is selected from the group consisting of hydrogen, —C$_1$-C$_{12}$ alkyl, —C$_2$-C$_{12}$ alkenyl, —C$_2$-C$_{12}$ alkynyl, —C$_3$-C$_{12}$ cycloalkyl, -aryl, -heteroaryl, -heterocyclic, —NH$_2$, —NH—C$_1$-C$_{12}$ alkyl, —NH—C$_2$-C$_{12}$ alkenyl, —NH—C$_2$-C$_{12}$-alkynyl, —NH—C$_3$-C$_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of disclosed compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasterisomers of disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

The compounds disclosed herein can exist in solvated as well as unsolvated forms with pharmaceutically acceptable solvents such as water, ethanol, and the like, and it is intended that disclosed compounds include both solvated and unsolvated forms. In one embodiment, a disclosed compound is amorphous or, in another embodiment, a single polymorph. In another embodiment, a disclosed compound is a mixture of polymorphs. In another embodiment, a disclosed compound is in a crystalline form.

Isotopically labeled compounds are also contemplated herein, which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{18}$F, and $^{36}$Cl, respectively. For example, a disclosed compound may have one or more H atom replaced with deuterium.

Certain isotopically labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly suitable for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be suitable in some circumstances. Isotopically labeled compounds can generally be prepared by following procedures analogous to those disclosed in the examples herein by substituting an isotopically labeled reagent for a non-isotopically labeled reagent.

In some embodiments one or more of the nitrogen atoms of a disclosed compound if present are oxidized to N-oxide.

Representative synthetic routes for the preparation of the compounds disclosed herein are provided throughout the Examples section. As will be understood by the skilled artisan, diastereomers can be separated from the reaction mixture using column chromatography.

Disclosed compounds may be also be prepared using methods described in the literature, including, but not limited to, *J. Med. Chem.* 2011, 54(13), 4350-64; *Russian Journal of Organic Chemistry,* 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, contemplated herein in an embodiment is a method of increasing CFTR activity in a subject comprising administering an effective amount of a disclosed compound. Also contemplated herein is a method of treating a patient suffering from a condition associated with CFTR activity comprising administering to said patient an effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount" of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, E56K, P67L, R74W, D110E, D110H, R117C, G178R, E193K, L206W, R347H, R352Q, A455E, S549R, G551S, D579G, S945L, S997F, F1052V, K1060T, A1067T, G1069R, R1070Q, R1070W, F1074L, G1244E, S1251N, S1255P, D1270N, G1349D, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; 4508F/W1204X; R553X/W1316X; W1282X/N1303K, 591Δ18/E831X, F508del/R117H/N1303K/3849+10kbC>T; 4303K/384; and DF508/G178R).

In certain embodiments, the mutation is a Class I mutation, e.g., a G542X; a Class II/I mutation, e.g., a ΔF508/G542X compound heterozygous mutation. In other embodiments, the mutation is a Class III mutation, e.g., a G551D; a Class II/Class III mutation, e.g., a ΔF508/G551D compound heterozygous mutation. In still other embodiments, the mutation is a Class V mutation, e.g., a A455E; Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

As discussed above, the disclosure also encompasses a method of treating cystic fibrosis. Methods of treating other conditions associated with CFTR activity, including conditions associated with deficient CFTR activity, comprising administering an effective amount of a disclosed compound, are also provided herein.

For example, provided herein is a method of treating a condition associated with deficient or decreased CFTR activity comprising administering an effective amount of a disclosed compound that enhances CFTR activity. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, cholestatic liver disease (e.g. Primary biliary cirrhosis (PBC) and primary sclerosing cholangitis (PSC)), dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, a disclosed method of treatment comprises administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), deuterated Ivacaftor, GLPG2851, GLPG2737, GLPG2451, VX-809 (3-(6-(1-(2, 2-difluorobenzo[d][1,3]dioxol-5-yl)cyclopropanecarbox-amido)-3-methylpyridin-2-yl)benzoic acid, deuterated lumacaftor, VX-661 (1-(2,2-difluoro-1,3-benzodioxol-5-yl)-N-[1-[(2R)-2,3-dihydroxypropyl]-6-fluoro-2-(2-hydroxy-1, 1-dimethylethyl)-1H-indol-5-yl]-cyclopropanecarboxam-ide), VX-983, VX-152, VX-440, VX-445, VX-659, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG2665, GLPG2222 (for example, a CFTR corrector); and compounds described in, e.g., WO2014/144860 and 2014/176553, hereby incorporated by reference. Non-limiting examples of modulators include QBW-251, QR-010, NB-124, riociquat, SPX-101, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agent and incorporated by reference. Non-limiting examples of anti-inflammatory agents include N6022 (3-(5-(4-(1H-imidazol-1-yl) phenyl)-1-(4-carbamoyl-2-methylphenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983, VX-152, VX-440, VX-445, VX-659, GLPG2222 and GLPG2665) or potentiator (e.g., ivacaftor, genistein, GLPG2545, GLPG3067, GLPG1837). In certain of these embodiments, one of the at least two additional therapeutic agents is a CFTR corrector (e.g., VX-809, VX-661, VX-983, VX-152, VX-445, VX-659, VX-440, GLPG2222, GLPG2851, GLPG2737 and/or GLPG3221) and the other is a CFTR potentiator (e.g., ivacaftor, genistein, GLPG2545, GLPG3067, GLPG1837). In certain of these embodiments, one of the at least two additional therapeutic agents is a CFTR corrector (e.g., GLPG2222, GLPG2851, GLPG2737, GLPG3221 or GLPG2665) and the other is a CFTR potentiator (e.g., GLPG183, GLPG2545, or GLPG3067). In certain of these embodiments, one of the at least two additional therapeutic agents is a CFTR corrector (e.g., VX-809, VX-152, VX-445, VX-659, VX-440 or VX-661) and the other is a CFTR potentiator (e.g., ivacaftor, GLPG1837, GLPG2545, or GLPG3067). In certain of these embodiments, at least one CFTR modulator is an agent that enhances read-through of stop codons (e.g., NB124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, VX-152, VX-440, VX-445, VX-659, GLPG2222, GLPG2665, GLPG2851, GLPG2737, GLPG3221, NB124, ataluren) and/or the other is a CFTR potentiator (e.g., ivacaftor, genistein, GLPG1837, GLPG2545 and GLPG3067); e.g., one of the at least two additional therapeutic agents is GLPG2222, GLPG2851 or GLPG2665, and the other is GLPG1837, GLPG2545, or GLPG3067; or one of the at least two additional therapeutic agents is VX-809 or VX-661, and the other is ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; 4508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120+1G>A Splice-site mutation in gene intron 16 |
| VI | Reduced due to protein instability | N287Y a A –>T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease, |
| WT/Δ508F | heterozygote | Unaffected |
| WT/3120+1 G>A | heterozygote | Unaffected |
| Δ508F/W1204X | compound heterozygote | No lung disease, pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, S549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g, ΔF508 mutation, as compared to administration of ivacaftor alone. Another combination therapy that includes a disclosed compound may also include an effective amount of a readthrough agent (e.g., ataluren, NB124) and an effect amount of disclosed compound that may act as an amplifier.

The phrase "combination therapy," as used herein, refers to an embodiment where a patient is co-administered a disclosed compound, a CFTR potentiator agent (e.g., ivacaftor GLPG1837, GLPG2545, or GLPG3067) and optionally, one or more CFTR corrector agent(s) (e.g, VX-661, VX-152, VX-440, VX-445, VX659, GLPG2222, GLPG2851, GLPG2737 OR GLPG3221 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

In an embodiment, contemplated methods may include for example, administering prodrugs of the compounds described herein, for example, prodrugs of a compound of Formula I or II or a pharmaceutical composition thereof.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al., *Nature Reviews Drug Discovery* 2008, 7, 255).

For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_{1-2})$alkylamino-$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino $(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxy)methyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

Also contemplated in certain embodiments is the use of clathrates of the compounds described herein, pharmaceutical compositions comprising the clathrates, and methods of use of the clathrates. Clathrates of a disclosed compound or a pharmaceutical composition thereof are also contemplated herein.

As discussed above, the disclosure also contemplates administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be suitable for treatment of a systemic disorder and oral administration may be suitable to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

Disclosed compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, or about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present disclosure, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The disclosure also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the disclosure contemplates s administering a disclosed compound e.g., Formula I or II that corrects protein misfolding, reduces protein aggregation, corrects or restores protein trafficking and/or affects protein degradation for the treatment of a condition associated with a dysfunction in proteostasis. In some aspects, a disclosed compound e.g., Formula I or II that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucosaminidase, α-galactosidase A, cysteine transporter, acid ceremidase, acid α-L-fucosidase, protective protein, cathepsin A, acid β-glucosidase, acid β-galactosidase, iduronate 2-sulfatase, β-L-iduronidase, galactocerebrosidase, acid β-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. The compounds of Formula I or II can be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, a disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, a treatment of a disease associated with a dysfunction in proteostasis is diabetes and/or complications of diabetes, including, but not limited to, diabetic retinopathy, cardiomyopathy, neuropathy, nephropathy, and impaired wound healing is contemplated.

In a further embodiment, a treatment of a disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration is contemplated.

In yet additional embodiments, a disclosed method is directed to treating a disease associated with a dysfunction in proteostasis, wherein the disease affects the respiratory system or the pancreas. In certain additional embodiments, a contemplated method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome.

Additional conditions associated with a dysfunction of proteostasis include hemoglobinopathies, inflammatory diseases, intermediate filament diseases, drug-induced lung damage and hearing loss. For example, provided herein are methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). In another embodiment, methods for treating hearing loss, such as noise-induced hearing loss, aminoglycoside-induced hearing loss, and cisplatin-induced hearing loss comprising administering a disclosed compound are provided.

Additional conditions include those associated with a defect in protein trafficking and that can be treated according to a disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The disclosure is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the disclosure.

Example 1: N-(4-(Azetidin-1-yl)-4-oxobutyl)-5-(4-fluorophenyl)isoxazole-3-carboxamide

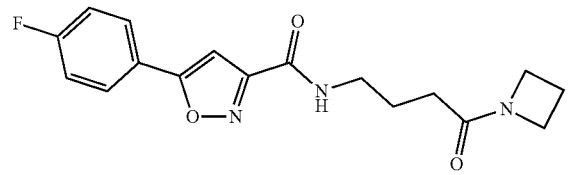
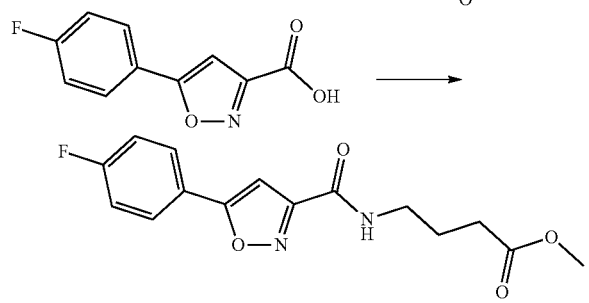

Step 1: Preparation of Methyl 4-(5-(4-Fluorophenyl)isoxazole-3-carboxamido)butanoate Into a 100 mL round-bottom flask was placed a solution of 5-(4-fluorophenyl)-1,2-oxazole-3-carboxylic acid (414 mg, 2.00 mmol) in N,N-dimethylformamide (20 mL). The solution was treated with methyl 4-aminobutanoate hydrochloride (462 mg, 3.01 mmol), HATU (1.9 g, 5.00 mmol) and diisopropylethylamine (903 mg, 6.99 mmol). The resulting mixture was allowed to stir at room temperature for 16 h, after which it was diluted with water (50 mL). The aqueous mixture was extracted with ethyl acetate (3×25 mL) and the combined organic extracts were washed with brine (3×50 mL). The organic phase was dried over $Na_2SO_4$ and concentrated under vacuum to afford 600 mg (98%) of methyl 4-(5-(4-fluorophenyl)isoxazole-3-carboxamido)butanoate as an orange solid. LC-MS (ES, m/z): [M+H]$^+$=307.

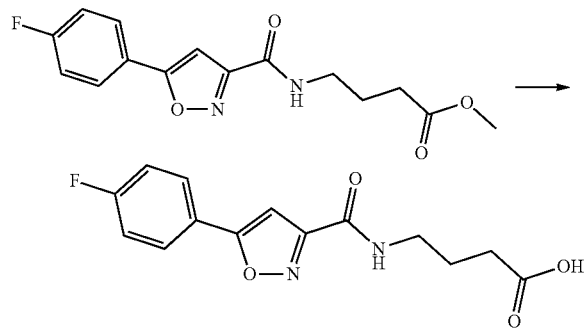

Step 2: Preparation of 4-(5-(4-Fluorophenyl)isoxazole-3-carboxamido)butanoic acid Into a 100 mL round-bottom flask was placed a solution of methyl 4-(5-(4-fluorophenyl)isoxazole-3-carboxamido)butanoate (612 mg, 2.00 mmol) in methanol (30 mL). The solution was cooled to 0° C. and then a separate solution of sodium hydroxide (400 mg, 10.00 mmol) in water (5 mL) was added in a dropwise manner. The resulting mixture was allowed to warm to room temperature and stir for 1 h before it was concentrated under vacuum. The remaining residue was diluted with water (20 mL) and the resulting aqueous mixture was washed with ethyl acetate (1×20 mL). The aqueous phase was treated with hydrogen chloride to adjust the pH of the mixture to a value of 2 and the resulting precipitate was collected by filtration. Drying of the solid afforded 450 mg (77%) of 4-(5-(4-fluorophenyl)isoxazole-3-carboxamido)butanoic acid as a white solid. LC-MS (ES, m/z): [M+H]$^+$=293.

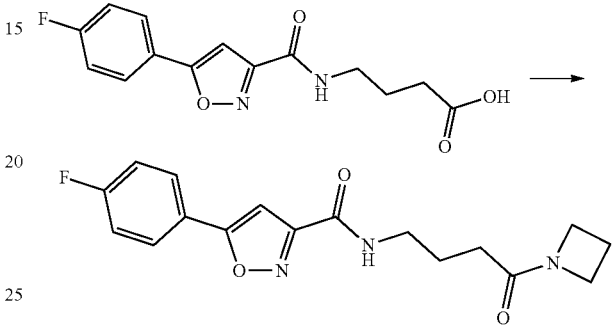

Step 3: Preparation of N-(4-(Azetidin-1-yl)-4-oxobutyl)-5-(4-fluorophenyl)isoxazole-3-carboxamide Into a 50 mL round-bottom flask was placed a solution of 4-(5-(4-fluorophenyl)isoxazole-3-carboxamido)butanoic acid (292 mg, 1.00 mmol) in N,N-dimethylformamide (10 mL). To the solution were added azetidine (114 mg, 2.00 mmol), HATU (950 mg, 2.50 mmol) and diisopropylethylamine (452 mg, 3.50 mmol). The resulting mixture was allowed to stir at room temperature for 16 h before it was diluted with water (10 mL). The aqueous mixture was extracted with ethyl acetate (2×25 mL) and the organic extracts were combined. The resulting solution was washed with brine (3×50 mL), dried over anhydrous sodium sulfate and concentrated under vacuum. The crude product was purified by preparative-HPLC with the following conditions: column: X Bridge C18 OBD Prep Column, 19 mm×250 mm; mobile phase: water (10 mmol/L $NH_4HCO_3$) and acetonitrile (32.0% acetonitrile up to 34.0% in 12 min); detector: UV 254/220 nm. This process afforded 103 mg (31%) of N-(4-(azetidin-1-yl)-4-oxobutyl)-5-(4-fluorophenyl)isoxazole-3-carboxamide as a white solid. LC-MS (ES, m/z): [M+H]$^+$=332. $^1$H NMR (300 MHz, CDCl$_3$): δ 7.82-7.76 (m, 2H), 7.46 (brs, 1H), 7.22-7.15 (m, 2H), 6.90 (s, 1H), 4.17 (brs, 4H), 3.52 (q, J=6.3 Hz, 2H), 2.32-2.23 (m, 4H), 2.04-1.92 (m, 2H).

Example 2: N-((1r,3r)-3-(Azetidine-1-carbonyl)cyclobutyl)-5-phenylisoxazole-3-carboxamide

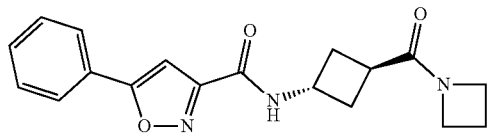

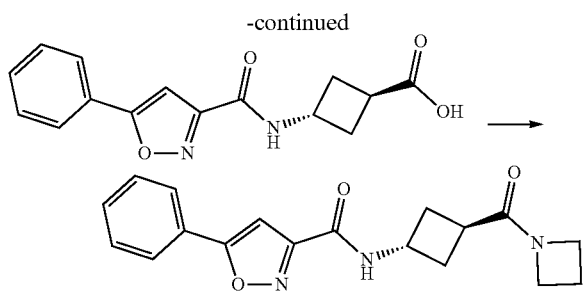

Preparation of N-((1r,3r)-3-(Azetidine-1-carbonyl) cyclobutyl)-5-phenylisoxazole-3-carboxamide Into a 100 mL round-bottom flask was placed a solution of (1r,3r)-3-(5-phenyl-1,2-oxazole-3-amido)cyclobutane-1-carboxylic acid (572 mg, 2.00 mmol) in N,N-dimethylformamide (20 mL). To the solution were added azetidine (228 mg, 3.99 mmol), HATU (1.52 g, 4.00 mmol) and diisopropylethylamine (774 mg, 5.99 mmol). The resulting mixture was allowed to stir at room temperature overnight before it was diluted with water (50 mL). The aqueous mixture was extracted with ethyl acetate (2×65 mL) and the organic extracts were combined. The organic extract was washed with brine (3×100 mL), dried over anhydrous sodium sulfate and concentrated under vacuum. The crude product was purified by re-crystallization from methanol to afford 103 mg (16%) of N-((1r,3r)-3-(azetidine-1-carbonyl)cyclobutyl)-5-phenylisoxazole-3-carboxamide as a white solid. LC-MS (ES, m/z): [M+H]$^+$=326. $^1$H NMR (300 MHz, CDCl$_3$): δ 9.15 (d, J=7.8 Hz, 1H), 7.95-7.92 (m, 2H), 7.58-7.54 (m, 3H), 7.36 (s, 1H), 4.52 (q, J=7.8 Hz, 1H), 4.03 (t, J=7.5 Hz, 2H), 3.86 (t, J=7.8 Hz, 2H), 3.01-2.93 (m, 1H), 2.41-2.30 (m, 4H), 2.27-2.18 (m, 2H).

Example 3: N-(4-(Azetidin-1-yl)-4-oxobutyl)-3-phenylisoxazole-5-carboxamide

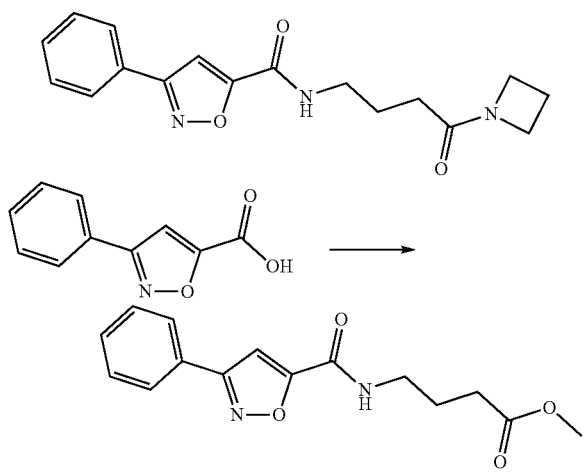

Step 1: Preparation of Methyl 4-(3-Phenylisoxazole-5-carboxamido)butanoate

Into a 100 mL round-bottom flask was placed a solution of 3-phenyl-1,2-oxazole-5-carboxylic acid (945 mg, 5.00 mmol) in N,N-dimethylformamide (20 mL). The solution was treated with methyl 4-aminobutanoate hydrochloride (925 mg, 6.02 mmol), HATU (2.85 g, 7.50 mmol) and diisopropylethylamine (1.94 g, 15.0 mmol). The resulting mixture was allowed to stir at room temperature overnight before it was diluted with water (50 mL). The aqueous mixture was extracted with ethyl acetate (2×100 mL) and the combined organic extracts were washed with brine (3×100 mL), dried over anhydrous sodium sulfate and concentrated under vacuum. The remaining residue was purified by column chromatography on silica gel, using ethyl acetate/petroleum ether (1:4) as the eluant, to afford 1.2 g (83%) of methyl 4-(3-phenylisoxazole-5-carboxamido)butanoate as a white solid. LC-MS (ES, m/z): [M+H]$^+$=289.

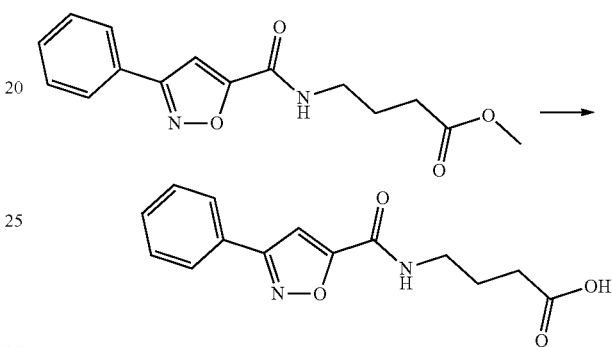

Step 2: Preparation of 4-(3-Phenylisoxazole-5-carboxamido)butanoic Acid

Into a 100 mL round-bottom flask was placed a solution of methyl 4-(3-phenylisoxazole-5-carboxamido)butanoate (1.16 g, 4.02 mmol) in methanol (20 mL). The solution was cooled to 0° C. and then treated with a separate solution of sodium hydroxide (800 mg, 20.0 mmol) in water (10 mL) in a dropwise fashion. The resulting mixture was allowed to warm to room temperature and then stir for 1 h. The reaction mixture was concentrated under vacuum and the remaining residue was diluted with water (20 mL). The aqueous mixture was washed with ethyl acetate (1×25 mL) and then treated with hydrogen chloride to adjust its pH to a value of 2. The precipitate that formed was collected by filtration, after which drying afforded 1.03 g (93%) of 4-(3-phenylisoxazole-5-carboxamido)butanoic acid as a white solid. LC-MS (ES, m/z): [M+H]$^+$=275.

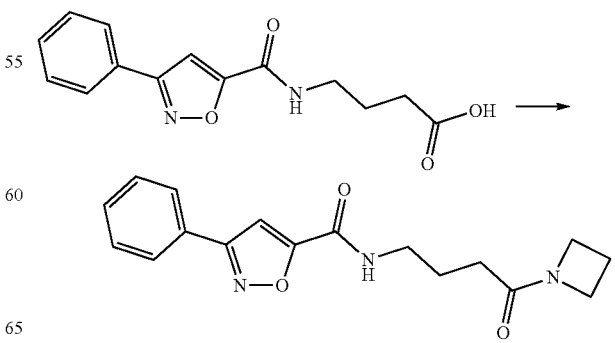

Step 3: Preparation of N-(4-(Azetidin-1-yl)-4-oxobutyl)-3-phenylisoxazole-5-carboxamide Into a 100 mL round-bottom flask was placed a solution of 4-[(3-phenyl-1,2-oxazol-5-yl)formamido]butanoic acid (548 mg, 2.00 mmol) in N,N-dimethylformamide (20 mL). The solution was treated with azetidine (228 mg, 3.99 mmol), HATU (1.52 g, 4.00 mmol) and diisopropylethylamine (774 mg, 5.99 mmol). The resulting mixture as allowed to stir at room temperature overnight before it was diluted with water (50 mL). The aqueous mixture was extracted with ethyl acetate (2×65 mL) and the combined organic extracts were washed with brine (3×100 mL), dried over anhydrous sodium sulfate and concentrated under vacuum. The crude product was purified by preparative-HPLC under the following conditions: column: X Bridge C18 OBD Prep Column, 19 mm×250 mm; mobile phase: water (10 mmol/L $NH_4HCO_3$) and acetonitrile (33.0% acetonitrile up to 50.0% in 7 min); detector: UV 254/220 nm. This process afforded 129 mg (21%) of N-(4-(azetidin-1-yl)-4-oxobutyl)-3-phenylisoxazole-5-carboxamide as a white solid. LC-MS (ES, m/z): $[M+H]^+$=314. $^1$H NMR (300 MHz, $CDCl_3$): δ9.03 (t, J=5.4 Hz, 1H), 7.95-7.90 (m, 2H), 7.62 (s, 1H), 7.56-7.52 (m, 3H), 4.08 (t, J=7.8 Hz, 2H), 3.81 (t, J=7.8 Hz, 2H), 3.27 (q, J=6.6 Hz, 2H), 2.21-2.06 (m, 4H), 1.79-1.72 (m, 2H).

Example 4: N-((1r,3r)-3-(Azetidine-1-carbonyl)cyclobutyl)-3-phenylisoxazole-5-carboxamide

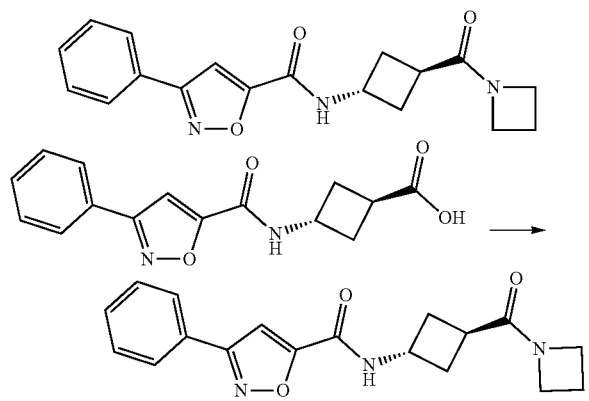

Preparation of N-(1r,3r)-3-(Azetidine-1-carbonyl)cyclobutyl)-3-phenylisoxazole-5-carboxamide Into a 100 mL round-bottom flask was placed a solution of (1r,3r)-3-(3-phenyl-1,2-oxazole-5-amido)cyclobutane-1-carboxylic acid (572 mg, 2.00 mmol) in N,N-dimethylformamide (20 mL). The solution was treated with azetidine (228 mg, 3.99 mmol), HATU (1.52 g, 4.00 mmol) and diisopropylethylamine (774 mg, 5.99 mmol). The resulting mixture was allowed to stir at room temperature overnight before it was diluted with water (50 mL). The aqueous mixture was extracted with ethyl acetate (2×65 mL) and the combined organic extracts were washed with brine (3×100 mL), dried over anhydrous sodium sulfate and concentrated under vacuum. The crude product was purified by re-crystallization from methanol to afford 124 mg (19%) of N-((1r,3r)-3-(azetidine-1-carbonyl)cyclobutyl)-3-phenylisoxazole-5-carboxamide as an off-white solid. LC-MS (ES, m/z): $[M+H]^+$=326. $^1$H NMR (300 MHz, $CDCl_3$): δ 9.30 (d, J=7.5 Hz, 1H), 7.95-7.91 (m, 2H), 7.64 (s, 1H), 7.55-7.52 (m, 3H), 4.50 (q, J=7.8 Hz, 1H), 4.04 (t, J=7.5 Hz, 2H), 3.86 (t, J=7.5 Hz, 2H), 3.02-2.96 (m, 1H), 2.44-2.27 (m, 4H), 2.25-2.17 (m, 2H).

Example 5: CFTR Activity Assays i. Ussing Measurements

As discussed above, Ussing measurements are used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilized, the chambers are clamped, and data is recorded by pulse readings every 5 seconds. Following baseline current stabilization, the following additions can be applied and the changes in current and resistance of the cells can be monitored.

1. Benzamil to the apical chamber to inhibit ENaC sodium channel
2. Forskolin to both chambers to activate ΔF508-CFTR by phosphorylation.
3. Genistein to both chambers to potentiate ΔF508-CFTR channel opening.
4. CFTRinh-172 to the apical chamber to inhibit ΔF508-CFTR Cl-conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% $CO_2$ for 24 hours. At the end of the treatment period, the media was changed to the Ieq experimental solution for 30 minutes before the experiment and plates are maintained in a $CO_2$-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:

1. The baseline $V_T$ and $G_T$ values were measured for approximately 20 minutes.
2. Benzamil was added to block ENaC for 15 minutes.
3. Forskolin plus VX-770 were added to maximally activate ΔF508-CFTR for 27 minutes.
4. Bumetanide was added to inhibit the NaK$_2$Cl cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples.

The results for hBE equivalent current ($I_{eq}$) measurements are shown below in Table 2. (** indicates activity ≥200% of VX-809 (3 uM) with compound at its EC$_{50}$ and VX-809 at 3 uM; * indicates activity 100-200% of VX-809 (3 uM) with compound at its EC$_{50}$ and VX-809 at 3 uM. ##indicates activity <100% of VX-809 (3 uM) with compound at its EC$_{50}$ and VX-809 at 3 uM. In Table 2, an $I_{eq}$ EC$_{50}$ value of "A" indicates the compound's EC$_{50}$ is ≤1 μM; an $I_{eq}$ EC$_{50}$ value of "B" indicates the compound's EC$_{50}$ is between 1 and 10 μM; an $I_{eq}$ EC$_{50}$ value of "C" indicates the compound's EC$_{50}$ is ≥10 μM.

TABLE 2

| Example # | Structure | $I_{eq}$ EC$_{50}$ | $I_{eq}$ Activity |
|---|---|---|---|
| 1 | 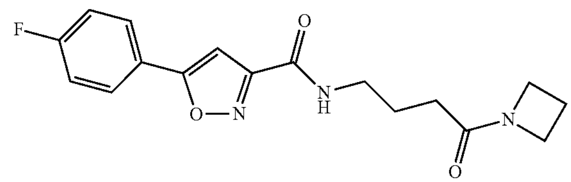 [SMILES: O=C(NCCCC(=O)N1CCC1)c1cc(-c2ccc(F)cc2)on1] | A | ** |
| 2 | 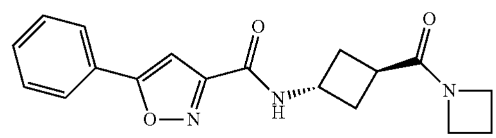 [SMILES: O=C(N[C@H]1C[C@H](C(=O)N2CCC2)C1)c1cc(-c2ccccc2)on1] | A | ** |
| 3 | 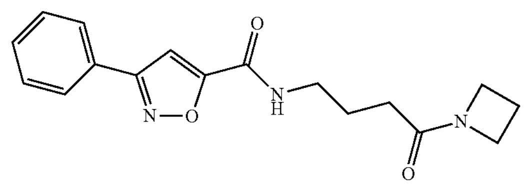 [SMILES: O=C(NCCCC(=O)N1CCC1)c1cc(-c2ccccc2)no1] | B | * |
| 4 | 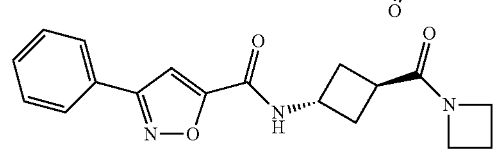 | B | ** |
| 5 | 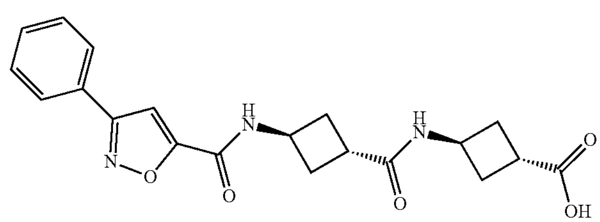 [SMILES: O=C(N[C@H]1C[C@H](C(=O)N[C@H]2C[C@H](C(=O)O)C2)C1)c1cc(-c2ccccc2)no1] | | |
| 6 | 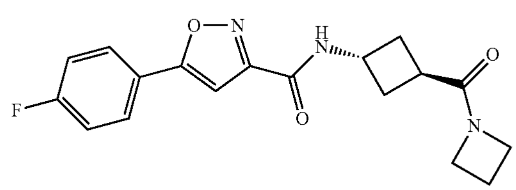 [SMILES: O=C(N[C@H]1C[C@H](C(=O)N2CCC2)C1)c1cc(-c2ccc(F)cc2)on1] | A | * |
| 7 | 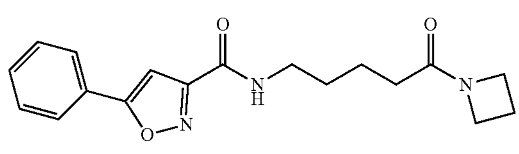 [SMILES: O=C(NCCCCC(=O)N1CCC1)c1cc(-c2ccccc2)on1] | A | * |

TABLE 2-continued

| Example # | Structure | $I_{eq}$ $EC_{50}$ | $I_{eq}$ Activity |
|---|---|---|---|
| 8 | 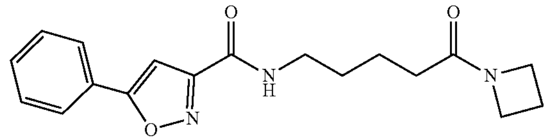 [SMILES: O=C(NCCCCC(=O)N1CCC1)c1cc(-c2ccccc2)on1] | A | ## |
| 9 | 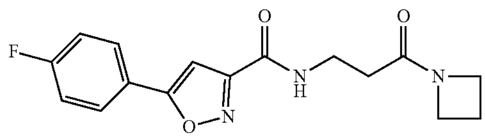 [SMILES: O=C(NCCC(=O)N1CCC1)c1cc(-c2ccc(F)cc2)on1] | | |
| 10 | 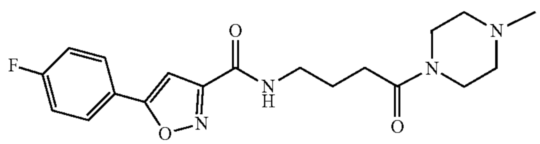 [SMILES: CN1CCN(C(=O)CCCNC(=O)c2cc(-c3ccc(F)cc3)on2)CC1] | A | ## |
| 11 | 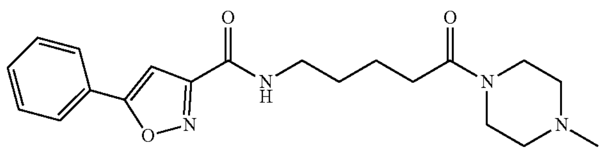 [SMILES: CN1CCN(C(=O)CCCCNC(=O)c2cc(-c3ccccc3)on2)CC1] | A | ## |
| 12 | 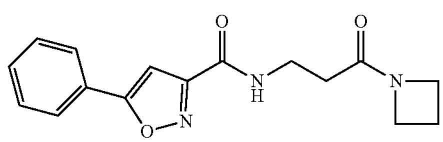 [SMILES: O=C(NCCC(=O)N1CCC1)c1cc(-c2ccccc2)on1] | A | * |

While this disclosure has been particularly shown and described with references to suitable embodiments thereof, it will be understood by those skilled in the art that various changes in form and details may be made therein without departing from the scope of the disclosure encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:
1. A compound represented by formula I or II:

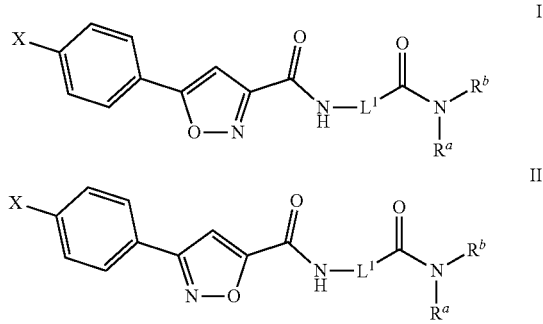

and pharmaceutically acceptable salts, stereoisomers, and prodrugs thereof, wherein:
X is selected from the group consisting of hydrogen and halogen;
$L^1$ is $C_{3-6}$cycloalkylene; and
$R^a$ and $R^b$ are each independently selected from the group consisting of hydrogen, $C_{1-4}$alkyl and $C_{3-6}$ cycloalkylene (optionally substituted by methyl, ethyl, or carboxyl); or $R^a$ and $R^b$ taken together with the nitrogen to which they are attached form a 4-6 membered heterocyclic ring containing one or more heteroatoms (O, S, or N), optionally substituted on additional ring nitrogen if present, by methyl or ethyl.

2. The compound of claim 1, wherein L¹ is C₄cycloalkylene.

3. The compound of claim 2, represented by formula III or IV:

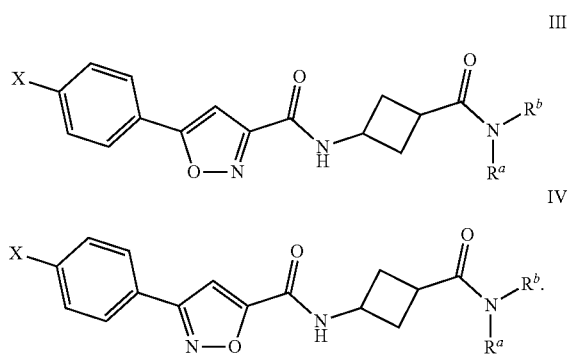

4. The compound of claim 1, wherein X is hydrogen or fluorine.

5. The compound of claim 1, wherein $R^a$ and $R^b$ taken together with the nitrogen to which they are attached form a 4 membered heterocyclic ring.

6. A compound selected from the group consisting of:

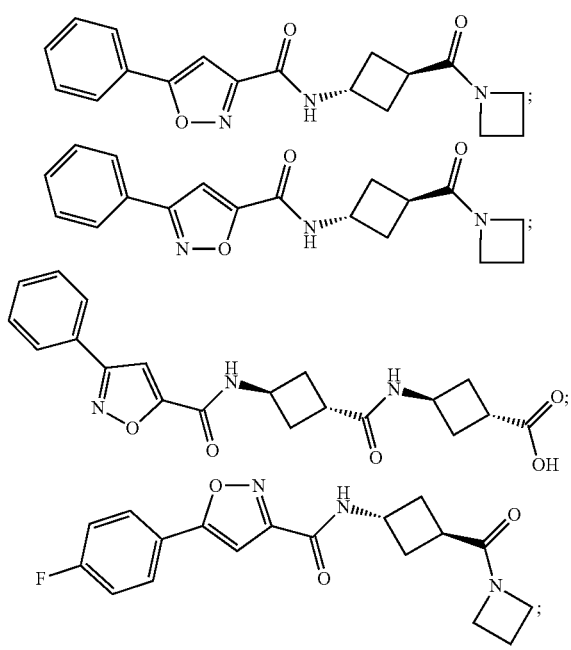

and pharmaceutically acceptable salts thereof.

7. A pharmaceutical composition comprising a compound of claim 1 and a pharmaceutically acceptable carrier or excipient.

8. The pharmaceutical composition of claim 7, wherein the composition further comprises at least one additional CFTR modulator.

9. The pharmaceutical composition of claim 7, wherein the composition further comprises at least two additional CFTR modulators.

10. A method of enhancing cystic fibrosis transmembrane conductance regulator (CFTR) activity in a subject in need thereof comprising administering to said subject an effective amount of a compound claim 1, wherein the subject is suffering from a disease associated with decreased CFTR activity and the disease is cystic fibrosis.

11. The method of claim 10, wherein the subject is a human patient.

12. The method of claim 11, further comprising administering at least one additional CFTR modulator.

13. The method of claim 12, wherein at least two additional CFTR modulators are administered.

14. The method of claim 12, wherein at least one CFTR modulator is a CFTR corrector or potentiator.

15. The method of claim 14, wherein each CFTR corrector or potentiator is independently selected from the group consisting of VX-770 (Ivacaftor), deuterated Ivacaftor, VX-809 (3-(6-(1-(2,2-difluorobenzo[d][1,3]dioxol-5yl)cyclopropanecarboxamido)-3-methylpyridin-2-yl)benzoic acid, deuterated lumacaftor, VX-661 ((R)-1-(2,2-difluorobenzo[d][1,3]dioxol-5-yl)-N-(1-2,3-dihydroxypropyl)-6-fluoro-2-(1-hydroxy-2-methylpropan-2-yl)-1H-indol-5-yl)cyclopropane-1-carboxamide), deuterated lumacaftor, genistein, VX-152, VX-440, VX-445, VX-659, GLPG2222, GLPG2665, GLPG2851, GLPG2737, GLPG2451, GLPG1837, GLPG3221, GLPG2545, GLPG3067, FDL169, and QBW-251.

16. The method of claim 15, wherein the CFTR corrector is selected from the group consisting of VX-809, VX-661, VX-152, VX-440, VX-445, VX-659, GLPG2222, GLPG2851, GLPG2737, GLPG3221 and VX-983 and the CFTR potentiator is selected from the group consisting of GLPG2451, GLPG1837, GLPG2545, GLPG3067, ivacaftor and genistein.

17. The method of claim 15, wherein one of the at least two additional therapeutic agents is a CFTR corrector and the other is a CFTR potentiator.

* * * * *